(12) United States Patent
Audiere et al.

(10) Patent No.: US 11,457,895 B2
(45) Date of Patent: Oct. 4, 2022

(54) METHOD FOR MEASURING A VISCOELASTIC PARAMETER OF A HUMAN OR ANIMAL ORGAN

(71) Applicant: ECHOSENS, Paris (FR)

(72) Inventors: Stéphane Audiere, Paris (FR); Laurent Sandrin, Bourg-la-Reine (FR)

(73) Assignee: ECHOSENS, Paris (FR)

( * ) Notice: Subject to any disclaimer, the term of this patent is extended or adjusted under 35 U.S.C. 154(b) by 169 days.

(21) Appl. No.: 16/320,386

(22) PCT Filed: Jul. 24, 2017

(86) PCT No.: PCT/EP2017/068687
§ 371 (c)(1),
(2) Date: Jan. 24, 2019

(87) PCT Pub. No.: WO2018/019791
PCT Pub. Date: Feb. 1, 2018

(65) Prior Publication Data
US 2019/0261950 A1    Aug. 29, 2019

(30) Foreign Application Priority Data

Jul. 25, 2016   (FR) ...................................... 1657126

(51) Int. Cl.
*A61B 8/08*        (2006.01)
*A61B 8/00*        (2006.01)
*G01S 7/52*        (2006.01)

(52) U.S. Cl.
CPC .............. *A61B 8/485* (2013.01); *A61B 8/085* (2013.01); *A61B 8/5223* (2013.01); *A61B 8/54* (2013.01);
(Continued)

(58) Field of Classification Search
CPC ....... A61B 8/485; A61B 8/085; A61B 8/5223; A61B 8/54; A61B 8/5207; A61B 8/08;
(Continued)

(56) References Cited

U.S. PATENT DOCUMENTS

2012/0065504 A1* 3/2012 Sandrin .................. A61B 8/485
                                                        600/438
2012/0190983 A1* 7/2012 Sandrin .................... A61B 8/42
                                                        600/442
(Continued)

FOREIGN PATENT DOCUMENTS

EP       1 169 636 A1     1/2002
EP       1 531 733 A2     5/2005
(Continued)

OTHER PUBLICATIONS

International Search Report as issued in International Patent Application No. PCT/EP2017/068687, dated Sep. 14, 2017.
(Continued)

*Primary Examiner* — Joseph M Santos Rodriguez
*Assistant Examiner* — Kaitlyn E Sebastian
(74) *Attorney, Agent, or Firm* — Pillsbury Winthrop Shaw Pittman LLP

(57) ABSTRACT

A method for measuring a viscoelastic parameter of an organ, includes emitting ultrasonic shots by an ultrasonic transducer; receiving by the transducer and recording the reflected ultrasonic signals; determining a viscoelastic parameter of the organ based on the recorded ultrasonic signals. The ultrasonic shots are formed by K groups of shots, separated temporally, K being greater than or equal to 1. Each K group is formed by the repetition, with a rate of PRF2, of MK blocks of ultrasonic shots, MK being greater than or equal to 1; each MK block is composed of N ultrasonic shots, N being greater than or equal to 1, PRF1
(Continued)

being the rate of emission of the N shots when N is chosen greater than 1; the N ultrasonic shots are distributed over P frequencies, P being between 1 and N, at least two ultrasonic shots belonging to two different blocks having different frequencies.

9 Claims, 7 Drawing Sheets

(52) U.S. Cl.
CPC ...... *G01S 7/52022* (2013.01); *G01S 7/52036* (2013.01); *A61B 8/5207* (2013.01); *G01S 7/52042* (2013.01)

(58) Field of Classification Search
CPC ..... A61B 8/44; A61B 8/4483; G01S 7/52036; G01S 7/52022; G01S 7/52042
See application file for complete search history.

(56) References Cited

U.S. PATENT DOCUMENTS

| | | | | |
|---|---|---|---|---|
| 2013/0024136 | A1* | 1/2013 | Gallippi | G01N 29/343 702/41 |
| 2015/0374338 | A1* | 12/2015 | Sandrin | A61B 8/485 600/438 |
| 2017/0296150 | A1* | 10/2017 | Rosenzweig | G01S 7/52022 |
| 2017/0367683 | A1* | 12/2017 | Zheng | G01S 7/52022 |
| 2018/0014814 | A1* | 1/2018 | Labyed | G16H 50/30 |

FOREIGN PATENT DOCUMENTS

| | | |
|---|---|---|
| EP | 2 477 551 A1 | 7/2012 |
| WO | WO 00/55616 A1 | 9/2000 |
| WO | WO 2004/016176 A2 | 2/2004 |
| WO | WO 2011/033050 A1 | 3/2011 |

OTHER PUBLICATIONS

International Preliminary Report on Patentability as issued in International Patent Application No. PCT/EP2017/068687, dated Oct. 31, 2018.

Nightingale, K., et al., "Derivation and analysis of viscoelastic properties in human liver: impact of frequency on fibrosis and steatosis staging", IEEE Transactions on Ultrasonics, Ferro Electrics and Frequency Control, IEEE, US, vol. 62, No. 1, Jan. 2, 2015 (Jan. 2, 2015), pp. 165-175.

Sasso, M., et al., "Liver Steatosis Assessed by Controlled Attenuation Parameter (CAP) Measured with the XL Probe of the FibroScan: A Pilot Study Assessing Diagnostic Accuracy", Ultrasound in Medicine and Biology, vol. 42, No. 1, Jan. 2, 2016 (Jan. 2, 2016), pp. 92-103.

* cited by examiner

METHOD FOR MEASURING A VISCOELASTIC PARAMETER OF A HUMAN OR ANIMAL ORGAN

CROSS REFERENCE TO RELATED APPLICATIONS

This application is the U.S. National Stage of PCT/EP2017/068687, filed Jul. 24, 2017, which in turn claims priority to French Patent Application No. 1657126 filed Jul. 25, 2016, the entire contents of all applications are incorporated herein by reference in their entireties.

FIELD OF THE INVENTION

The present invention concerns the field of measurement of the viscoelastic properties of a biological tissue. More specifically, the invention relates to a method for measuring a viscoelastic parameter using multi-frequency ultrasound pulses.

STATE OF THE ART

Several non-invasive techniques for measuring the viscoelastic properties of human or animal organs have been developed.

Of these techniques, pulse elastography is particularly effective in monitoring infections in soft tissues, and particularly the human liver. For example, the applicant has developed and marketed a device, Fibroscan™, which is now a reference for diagnosing and monitoring hepatic fibrosis. This device is illustrated, in particular, in patents EP 1 169 636 and EP 1 531 733 filed by the applicant. This infection can be the consequence of illnesses such as hepatitis or cancer of the liver, and it is characterised by a loss of elasticity of the liver. The technology developed by the applicant and described in the cited patents is known by the name "Vibration Controlled Transient Elastography" (or VCTE).

VCTE technology relates to the monitoring of the propagation of a shear wave within the tissue to be characterised. The shear wave is generated with the assistance of mechanical vibration, and its propagation is monitored using ultrasound signals. Monitoring of the propagation of the shear wave enables its speed of propagation to be measured, which depends directly on the elasticity of the propagation medium.

Other infections of the liver are currently more difficult to assess. This is the case, for example with hepatic steatosis, which is manifested by an accumulation of lipids in the cells of the liver, called hepatic cells. In certain cases this is a benign and reversible situation. However, it can be associated with a chronic inflammation (hepatic steatosis), in particular when it is accompanied by high alcohol consumption, obesity or metabolic illnesses. In chronic illnesses of the liver steatosis can be a co-factor in the growth of the fibrosis.

Liver steatosis can be assessed by measuring the absorption of the ultrasound signals which are propagated within the liver (see, for example, M. Sasso et al "*Controlled attenuation parameter (cap): a novel vcte guided ultrasound attenuation measurement for the evaluation of hepatic steatosis: preliminary study and validation in a cohort of patients with chronic liver disease from various causes*" in *Ultrasound in Medicine and Biology* Vol. 36, Issue 11, 2010, and M. Sasso et al. "*Liver steatosis assessed by controlled attenuation parameter (cap) measured with the xl probe of the fibroscan: a pilot study assessing diagnostic accuracy*" in *Ultrasound in Medicine and Biology*, Volume 42, Issue 1, 2015).

It is therefore important to be able to measure the quantity of steatosis present in the liver, and if possible to associate an assessment of the elasticity of the liver with the measurement of steatosis. These diagnoses must preferably be able to be undertaken during the same medical consultation, using non-invasive techniques.

Advantageously, these attenuation measures are coupled with measurement of another viscoelastic property of the liver, such as for example its elasticity. This technique is described by patent application EP2477551 filed by the applicant.

However, the known technical solutions provide measurements with a signal-to-noise ratio which can be very low, particularly in the case of obese patients—whose livers often have steatosis—due to the high attenuation of the ultrasound pulses in the subcutaneous tissues (in particular fat), and in the medium to be measured itself.

SUMMARY OF THE INVENTION

In this context the present invention seeks to provide a method for measuring at least one property of a human or animal organ or of a viscoelastic tissue enabling reliable, reproducible measurements to be made rapidly with a higher signal-to-noise ratio in a large cohort of patients also including obese patients.

To this end, the invention proposes, in particular, a method for measuring at least one viscoelastic parameter of a human or animal organ, wherein said method includes the following steps:
  emission by an ultrasound transducer of a plurality of ultrasound shots, wherein said ultrasound shots are propagated in the organ to be characterised;
  reception by the ultrasound transducer and recording of the reflected ultrasound signals;
  determination of at least one viscoelastic parameter of the organ from the recorded ultrasound signals.
In the method according to the invention:
  the plurality of ultrasound shots is formed by the repetition of K groups of shots, wherein said groups are separated over time, and wherein K is greater than or equal to 1;
  each of the K groups of ultrasound shots is formed by the repetition at a rate (Pulse Repetition Frequency) PRF2 of MK set(s) of ultrasound shots, wherein Mk is greater than or equal to 1;
  each of the said MK sets consists of N ultrasound shots, wherein N is greater than or equal to 1, and wherein PRF1 is the rate of emission of the N shots when N is chosen to be greater than 1;
  the N ultrasound shots are distributed over P frequencies, wherein P is between 1 and N, and wherein at least two ultrasound shots belong to two different sets with different frequencies The expression "viscoelastic parameter of a human or animal organ" is understood to mean a parameter such as, for example, the attenuation of the ultrasound signals. In the case of the human liver this parameter is related to steatosis, i.e. the concentration of lipids in the tissues.

The expression "human or animal organ" is understood to mean a biological tissue such as, for example, the liver. In what follows this biological tissue will be called a human or animal organ or, indiscriminately, a viscoelastic tissue or medium.

The expression "ultrasound transducer" is understood to mean a device positioned close to the tissue to be studied, and capable both of emitting ultrasound signals which are propagated within the tissue, and of detecting the reflected ultrasound signals. The transducer can also be formed by a multiplicity of elements intended to form a strip.

Advantageously, in the case of the human liver, the invention enables an improved assessment of steatosis to be obtained by increasing the quality, reproducibility and speed of the measurements.

According to one implementation, the reflected ultrasound signals can be recorded with each emitted ultrasound shot.

The method according to the invention makes provision for the emission of a multiplicity of ultrasound shots distributed into K groups, wherein the K groups are separated over time. Each of the K groups includes a repetition of $M_K$ sets of ultrasound shots, at a rate PRF2. The expression "rate PRF2" is understood to mean the rate of repetition of the emission of the M sets of ultrasound shots. For example, a rate PRF2 of 1 Hz comprises the emission of one set of shots per second, and a rate PRF2 of 60 Hz comprises the emission of 60 sets of shots per second, i.e. one set every 1/60th of a second.

Each of the $M_K$ sets emitted consists of N shots. The N shots composing each set are emitted at a rate, i.e. a rate of repetition, PRF1.

When an ultrasound pulse is propagated within the tissue to be characterised, its intensity according to the distance travelled z is given by the following formula:

$$I(z) = I_0 e^{-\alpha(f)z}$$

In this formula I(z) is the intensity of the pulse according to the distance travelled z, $I_0$ is the intensity emitted and $\alpha(f)$ is the coefficient of absorption of the tissue, expressed in dB m$^{-1}$. The coefficient of absorption depends on several parameters, and in particular on the frequency of the ultrasound signals, f, and on the properties of the tissue. More specifically, in the case of the liver, $\alpha(f)$ depends on the lipid content of the tissue, and therefore constitutes a measurement of steatosis.

The N ultrasound shots are distributed over P frequencies. The P frequencies are different when P>1. This enables advantage to be taken of the fact that the ultrasound transducer used to implement the method can emit pulses with different central frequencies.

All the frequencies which an ultrasound transducer can emit are called the transducers bandwidth. The invention therefore enables reflected ultrasound signals to be measured at several frequencies, and therefore enables $\alpha(f)$ to be measured for different values of f.

One advantage of the invention is that it increases the measured signal, since several pulses at different frequencies are sent into the tissue. Measurements with a higher signal-to-noise ratio are then made. In addition, this increase of the signal-to-noise ratio is accomplished without increasing the intensity associated with each pulse: the total transmitted power is shared by several pulses spread over a wide range of frequencies. The range of accessible frequencies is the bandwidth of the ultrasound transducer.

In the case of the human liver, the reference frequency to measure steatosis is 3.5 MHz (central frequency). In a range of several MHz around this frequency, coefficient $\alpha(f)$ varies approximately linearly with frequency f.

By virtue of the invention it is possible to measure $\alpha(f)$ with a better signal-to-noise ratio for several values of f around the central frequency of 3.5 MHz and, using for example a simple linear regression, to obtain a more precise estimate of reference value $\alpha(f=3.5$ MHz).

In addition to the main characteristics mentioned above, the method for measuring at least one property of a biological tissue according to the invention may have one or more additional characteristics below, considered individually or in all technically possible combinations:
- the measured viscoelastic parameter is an ultrasound attenuation parameter;
- rate PRF2 is greater than or equal to 1 Hz and rate PRF1 is greater than or equal to 1 kHz;
- the different frequencies P and the spectral widths of the N ultrasound shots are chosen such that they roughly cover the bandwidth of the ultrasound transducer;
- P is equal to N;
- M is between 10 and 10000, P is between 1 and 11, N is between 2 and 11, PRF2 is between 5 Hz and 500 Hz and PRF1 is between 1 kHz and 10 kHz;
- Fc is the central frequency of the ultrasound transducer, P is equal to 5 and the chosen frequencies are 0.5\*Fc<F1<0.7\*Fc; 0.7\*Fc<F2<0.9\*Fc; 0.9\*Fc<F3<1.1\*Fc; 1.1\*Fc<F4<1.3\*Fc; 1.3\*Fc<F5<1.5\*Fc;

Another purpose of the present application is a device to implement the method, wherein said device includes:
- an ultrasound transducer able to emit and receive ultrasound signals, in real time, and able to be positioned in contact with an outside surface of the viscoelastic medium;
- means of control of said ultrasound transducer for the emission of a plurality of ultrasound shots, wherein said plurality of ultrasound shots is formed by K groups of shots, wherein said groups are separated over time, wherein K is greater than or equal to 1, wherein each of the K groups of ultrasound shots is formed by the repetition at a rate PRF2 of $M_K$ group(s) of ultrasound shots, and wherein $M_K$ is greater than or equal to 1; wherein each of the said $M_K$ sets is composed of N ultrasound shots, wherein N is greater than or equal to 1, and wherein PRF1 is the rate of emission of the N shots when N is chosen to be greater than 1; wherein the N ultrasound shots are distributed over P frequencies, wherein P is between 1 and N, and wherein at least two ultrasound shots belong to two different sets with different frequencies;
- means of recording and processing the reflected ultrasound signals able to determine at least one viscoelastic parameter of the organ.

Another purpose of the present application is a second method including the following steps:
- measurement of a viscoelastic parameter of a human or animal organ by pulse elastography;
- measurement of a parameter of attenuation of the ultrasound signals with the method according to the invention described in the previous paragraphs.

Another purpose of the present invention is a device to implement the second method, including:
- a vibrator able to apply to a human or animal organ a low-frequency pulse to generate a shear wave;
- a probe including at least one ultrasound transducer able to emit and receive ultrasound signals, in real time, and able to be positioned in contact with an outside surface of the viscoelastic medium;
- means of control of said probe for the emission of a plurality of ultrasound shots, wherein said plurality of ultrasound shots is formed by K groups of shots, wherein said groups are separated over time, wherein K is greater than or equal to 1, wherein each of the K groups of ultrasound shots is formed by the repetition at a rate PRF2 of $M_K$ group(s) of ultrasound shots, and wherein $M_K$ is greater than or equal to 1; wherein each of the said $M_K$ sets is composed of N ultrasound shots, wherein N is greater than or equal to 1, and wherein PRF1 is the rate of emission of the N shots when N is chosen to be greater than 1; wherein the N ultrasound shots are distributed over P frequencies, wherein P is between 1 and N, and wherein at least two ultrasound shots belong to two different sets with different frequencies;

means of recording and processing the reflected ultrasound signals able to determine at least one viscoelastic parameter of the organ.

LIST OF FIGURES

Other characteristics and advantages of the invention will be made clear from the description given of it below, by way of example and non-restrictively, with reference to the figures appended hereto, in which.

DETAILED DESCRIPTION OF THE INVENTION

Figure 1:
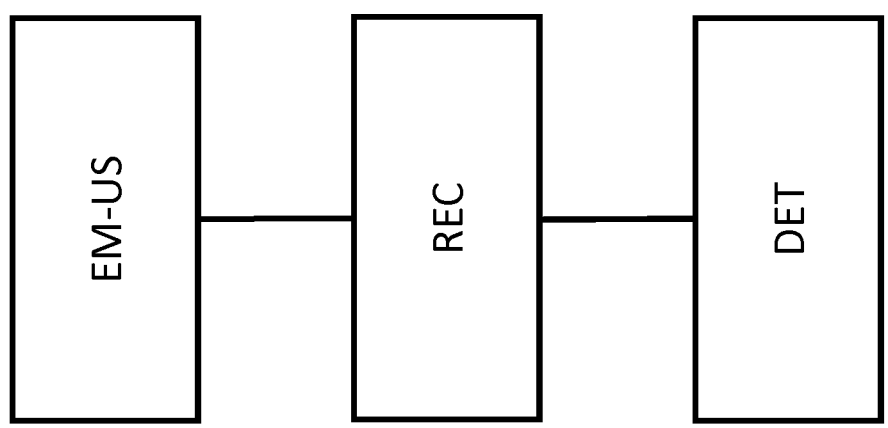
FIG. 1 shows the different steps of the first method of the invention.
Figure 1:

FIG. 1 illustrates the different steps of first method 1 of the invention. Method 1 in this case includes three steps:

an emission EM-US by an ultrasound transducer US of a plurality of ultrasound shots, which are propagated in the organ to be characterised, a recording REC by the same ultrasound transducer US of the reflected ultrasound signals, a determination DET of at least one viscoelastic parameter of the organ from the recorded signals.

Advantageously, this implementation enables a parameter such as the attenuation of the ultrasound signals to be measured. This parameter is particularly significant in the case of the human liver since it is related to the presence of steatosis. The structure and characteristics of the plurality of ultrasound shots are represented in FIGS. 2 and 3.

Figure 2:
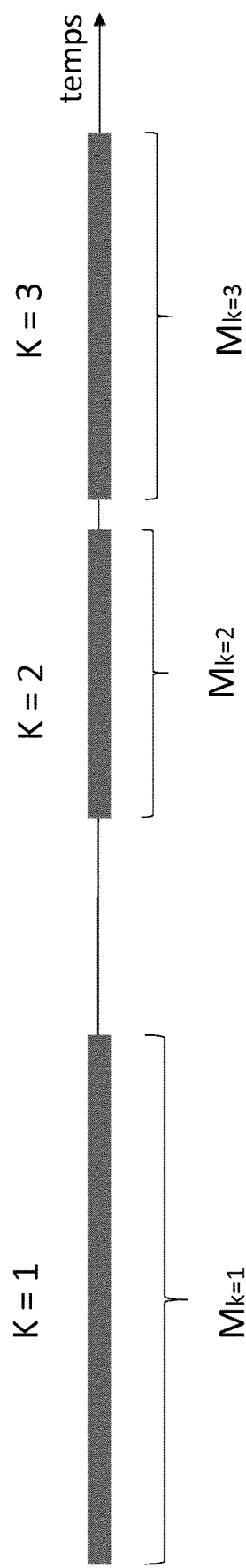
FIG. 2 illustrates a plurality of ultrasound shots formed, for example, by K=3 groups, wherein the three groups K=1, K=2 and K=3 are formed respectively by $M_{K=1}$, $M_{K=2}$ and $M_{K=3}$ sets of shots.
Figure 3:
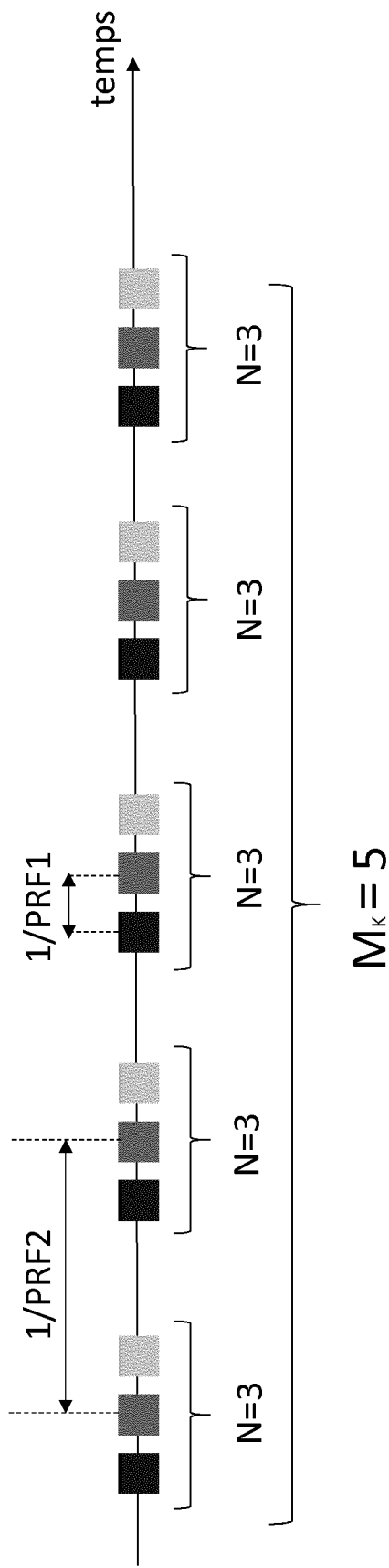
FIG. 3 shows the structure of one of the K groups of ultrasound shots of FIG. 2; as an example, this group is formed by $M_K$=5 sets of shots, wherein said sets are emitted at a rate PRF2, wherein each of the $M_K$ sets is formed by N ultrasound shots, and wherein said N shots are emitted at a rate PRF1.

FIG. 2 shows that the plurality of shots is formed by K groups of ultrasound shots. For example, in the case shown in FIG. 2, there are K=3 groups of ultrasound shots.

Each of the K groups is formed by a variable number of sets of ultrasound shots. The number of blocks of shots forming group K is indicated with the letter $M_K$. The three groups represented in FIG. 2 are formed respectively by $M_{K=1}$, $M_{K=2}$ and $M_{K=3}$ sets of shots, respectively.

FIG. 2 also shows that the K groups of ultrasound shots are separate over time, and they can be emitted at a variable rate, wherein the time difference between the end of one group and the start of the next is not fixed.

One advantage of this implementation is that it ensures a large variety of possible sequences of ultrasound shots.

Each of the K groups of ultrasound shots is formed by the repetition at a rate PRF2 of $M_K$ set(s) of ultrasound shots, wherein $M_K$ is greater than or equal to 1.

FIG. 3 shows the structure of one of the K groups formed, as an example, by $M_K$=5 sets of ultrasound shots.

As can be seen in FIG. 3, the time distance between one set and the next set is equal to 1/PRF2. PRF2 is therefore the rate of repetition at which the sets are emitted.

Each of the said $M_K$ sets consists of N ultrasound shots, wherein N is greater than or equal to 1, and wherein PRF1 is the rate of emission of the N shots when N is chosen to be greater than 1. As can be seen in FIG. 3, the N=3 ultrasound shots are emitted at a fixed rate equal to 1/PRF1. In addition, the N ultrasound shots forming one of the $M_K$ sets are distributed over P frequencies, wherein P is between 1 and N. In the case illustrated in FIG. 3 the N=3 ultrasound shots are distributed over P=3 different frequencies.

FIG. 3 illustrates that at least two ultrasound shots belonging to two different sets have two different frequencies. For example, the first shot of the first set and the second shot of the second set have two different frequencies.

The advantage of this implementation is that it emits ultrasound pulses distributed over several frequencies. This enables P values of ultrasound attenuation parameter $\alpha(f)$ to be measured, one for each of the P frequency values, and a more precise and reproducible ultrasound attenuation measurement to be obtained. Function $\alpha(f)$ is the coefficient of absorption of the tissue as a function of ultrasound frequency f, expressed in dB m$^{-1}$.

In the case of the human liver, one advantage of this implementation is that it enables steatosis to be assessed more precisely and more reproducibly.

According to one implementation of the invention, rate PRF2 is greater than or equal to 1 Hz and rate PRF1 is greater than or equal to 1 kHz.

One advantage of this implementation is that it uses a high rate PRF1, which enables the tissue to be probed with several ultrasound shots before the medium moves, for example due to the patient's respiration. Moreover, a high rate PRF2 also enables measurements with a satisfactory signal-to-noise ratio to be obtained, whilst using shorter acquisition periods, which is an advantage for applications in a medical context.

According to one implementation of the intervention, frequencies P are different, and the spectral widths of the N ultrasound shots are chosen such that they roughly cover the bandwidth of ultrasound transducer US.

One advantage of this implementation is that it distributes the pulses over a spectrum able to cover the transducers entire bandwidth, and therefore that it maximises the signal-to-noise ratio whilst reducing the period of the acquisition.

According to one particular implementation of the invention, P is equal to 1. In this case the N shots in the same set have the same frequency, but shots belonging to different sets have different frequencies.

One advantage of this implementation is that it puts ultrasound shots with the same frequency in the same set.

According to another implementation of the invention P is equal to N.

In this implementation each of the N pulses forming a set has a different central frequency, which is advantageous to use the transducers entire bandwidth, and to maximise the signal-to-noise ratio.

According to one implementation of the invention, M is between 10 and 10000, P is between 2 and 5, N is between 2 and 5, PRF2 is between 5 Hz and 500 Hz and PRF1 is between 3 kHz and 10 kHz.

According to one implementation, Fc is the central frequency of the ultrasound transducer, P is equal to 5 and the chosen frequencies are $0.5*Fc<F1<0.7*Fc$, $0.7*Fc<F2<0.9*Fc$, $0.9*Fc<F3<1.1*Fc$, $1.1*Fc<F4<1.3*Fc$, $1.3*Fc<F5<1.5*Fc$.

One advantage of this implementation is that ranges of values are chosen for the central frequencies of the ultrasound pulses wherein these ranges are able to cover the transducers bandwidth. This enables the signal-to-noise ratio to be maximised for a given bandwidth of the transducer.

For example, if Fc=3.5 MHz the ranges of values according to this implementation advantageously cover the bandwidth of the transducer forming probe M of the Fibroscan™.

Figure 4:
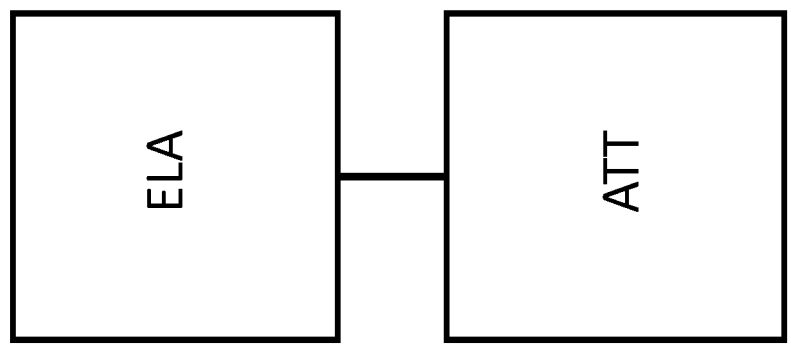
FIG. 4 shows the different steps of the second method of the invention.

FIG. 4 illustrates the different steps of the second method according to invention 60 of measurement of at least one viscoelastic parameter of a human or animal organ (cf. reference 5 of FIG. 6 described below), wherein said method includes the following steps:
- measurement ELA of a viscoelastic parameter of the liver by pulse elastography;
- measurement ATT of a parameter of attenuation of the ultrasound signals with method 1 of FIG. 1;

The term "pulse elastography" is understood to mean a technique of the "Vibration Controlled Transient Elastography", or VCTE, type. With this technology, implemented in the Fibroscan™, it is possible to measure, non-invasively, the elasticity of a biological tissue as it is described, for example, in patents EP 1 169 636 and EP 1 531 733.

Step ELA therefore consists in mechanically generating a shear wave which is propagated inside the tissue to be characterised. Propagation of the shear wave is then followed by emitting ultrasound pulses in the tissue. Due to the ultrasound signals reflected by the medium, the movements caused in the tissue by the shear wave are measured. By sending sequences of ultrasound signals it is possible to measure the speed of propagation of the shear wave, which relates to the elasticity of the medium.

Step ATT consists in implementing method 1 described by the present application, and illustrated by FIG. 1.

Method 60 according to this implementation is particularly advantageous since it enables two viscoelastic parameters to be measured, namely the elasticity and the ultrasound attenuation, with a single performance of method 60.

Another advantage of method 60 in the case of the human liver is systematically to associate a measurement of elasticity of the tissue with an assessment of the ultrasound attenuation, which can be particularly useful to assess the progress of the fibrosis and of the steatosis.

Figure 5:
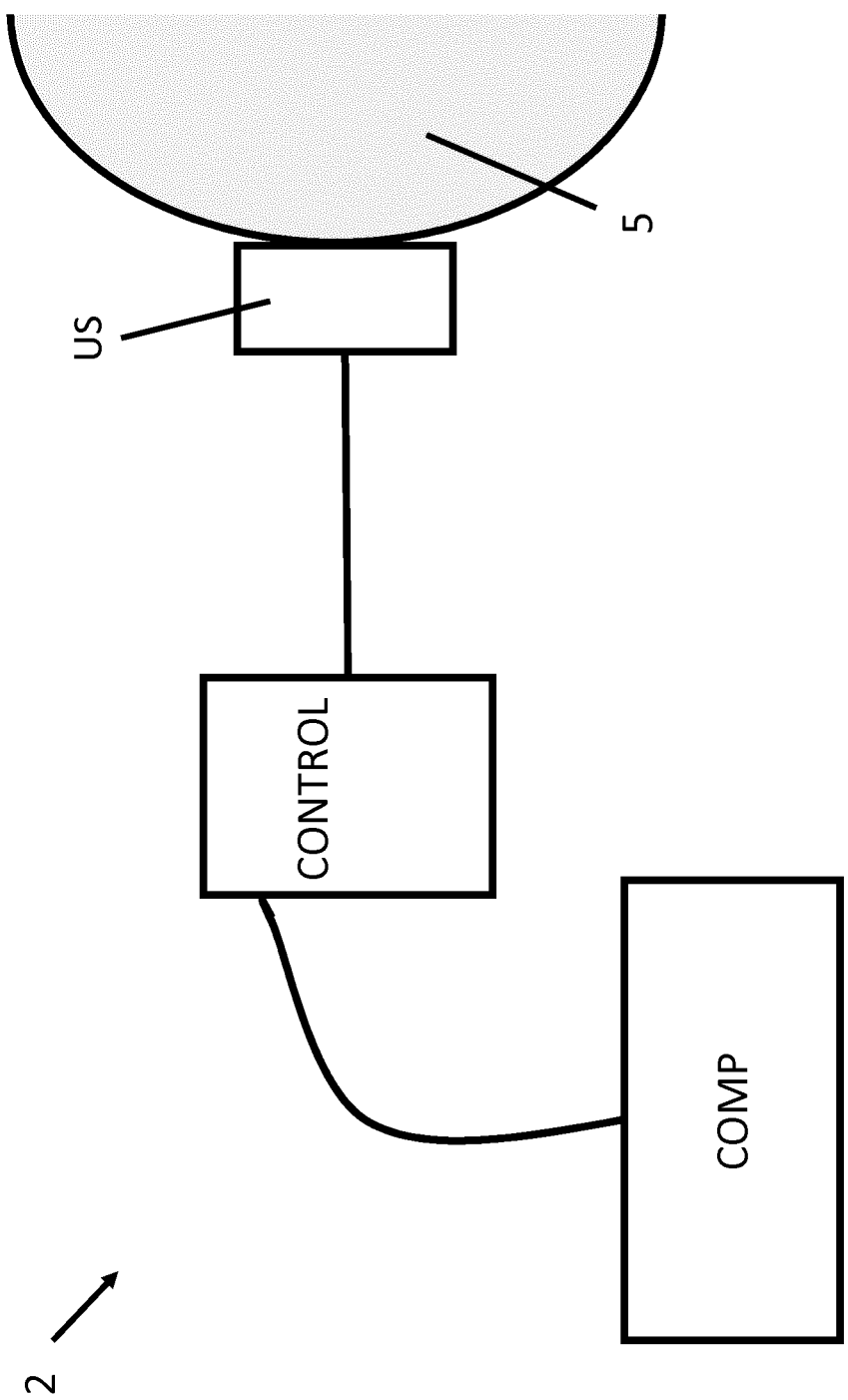
FIG. 5 illustrates diagrammatically a device for the implementation of the method of FIG. 1.

FIG. 5 illustrates diagrammatically an example of device 2 to implement method 1 according to the invention of FIG. 1. This device includes:
- an ultrasound transducer US able to emit and receive ultrasound signals, in real time, and which can be positioned in contact with an outside surface of a viscoelastic medium 5;
- means of control CONTROL of said ultrasound transducer US for the emission of a plurality of ultrasound shots, wherein said plurality of ultrasound shots is formed by K groups of shots, wherein said groups are separated over time, wherein K is greater than or equal to 1, wherein each of the K groups of ultrasound shots is formed by the repetition at a rate PRF2 of $M_K$ group(s) of ultrasound shots, and wherein $M_K$ is greater than or equal to 1; wherein each of the said $M_K$ sets is composed of N ultrasound shots, wherein N is greater than or equal to 1, and wherein PRF1 is the rate of emission of the N shots when N is chosen to be greater than 1; wherein the N ultrasound shots are distributed over P different frequencies, and wherein P is between 1 and N;
- means COMP of recording and processing the reflected ultrasound signals able to determine at least one viscoelastic parameter of organ 5.

Transducer US is used to emit the ultrasound pulses being propagated in the liver. This transducer is designed for the emission of ultrasound pulses with several central frequencies, and it is positioned close to tissue 5. Transducer US also acts as a sensor for the reflected ultrasound signals.

Means of control CONTROL act so as to control transducer US to emit a sequence of multi-frequency ultrasound pulses. The parameters of the sequence, namely PRF1, PRF2, $M_K$, N, P and the values of the central frequencies of the pulses, are chosen by the operator and implemented through means CONTROL.

Means COMP of recording and processing the reflected ultrasound signals enable the attenuation parameters to be calculated from the recorded data. The ultrasound attenuation coefficient, or parameter $\alpha(f)$, may for example be calculated using the algorithm for obtaining the Controlled Attenuation Parameter (or CAP).

For example, means CONTROL and COMP can be incorporated in a computer or any programmed device, which would enable, simultaneously, the parameters of the sequence of ultrasound pulses to be programmed, device 2 to be actuated and controlled, and the data to be recorded and processed.

Advantageously, this device enables multi-frequency ultrasound pulses to be emitted and their attenuation to be measured according to method 1. Device 2 therefore enables $\alpha(f)$ to be measured for several values of central frequency f of the pulses. In the case of the human liver, this enables a more precise and reliable evaluation of the steatosis of the liver, i.e. of the concentration of lipids in the tissue.

Figure 6:
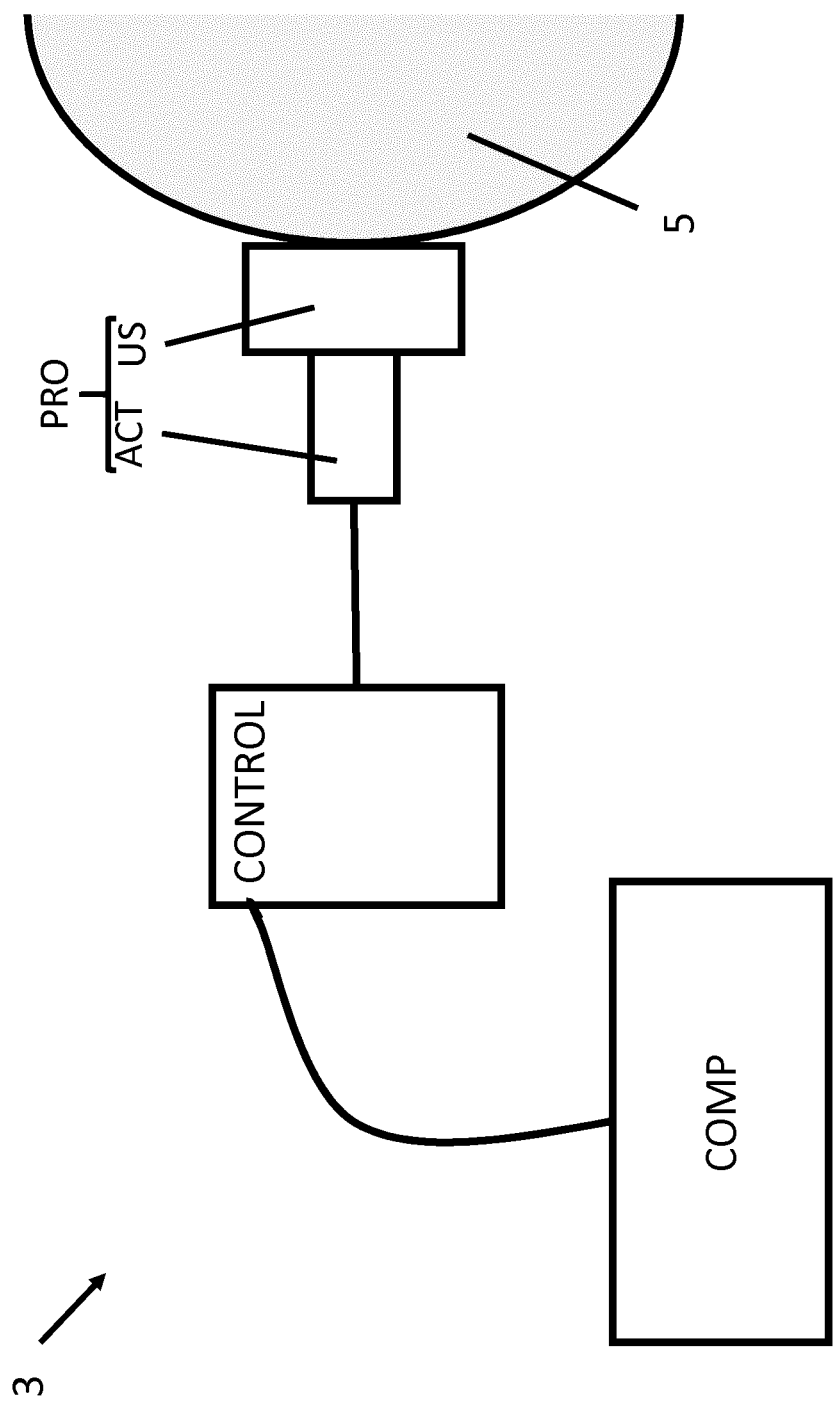
FIG. 6 illustrates diagrammatically a device for the implementation of the method of FIG. 4.

FIG. 6 illustrates schematically an example of a device 3 for implementing method 60 illustrated by FIG. 4. Device 3 includes:
- a vibrator ACT able to apply to a human or animal organ 5 a low-frequency pulse to generate a shear wave;
- a probe PRO including at least one ultrasound transducer able to emit and receive ultrasound signals, in real time, and able to be positioned in contact with an outside surface of viscoelastic medium 5;
- means of control CONTROL of said probe PRO for the emission of a plurality of ultrasound shots, wherein said plurality of ultrasound shots is formed by K groups of shots, wherein said groups are separated over time, wherein K is greater than or equal to 1, wherein each of the K groups of ultrasound shots is formed by the repetition at a rate PRF2 of MK group(s) of ultrasound shots, and wherein $M_K$ is greater than or equal to 1, wherein each of the said $M_K$ sets is composed of N ultrasound shots, wherein N is greater than or equal to 1, and wherein PRF1 is the rate of emission of the N shots when N is chosen to be greater than 1; wherein the N ultrasound shots are distributed over P different frequencies, and wherein P is between 1 and N;

means COMP of recording and processing the reflected ultrasound signals able to determine at least one viscoelastic parameter of organ 5.

Device 3 enables method 60 according to the invention to be implemented, and therefore two viscoelastic parameters of the tissue to be measured. For example, the first viscoelastic parameter may be a parameter describing the propagation of a shear wave in the tissue, and the second a parameter of attenuation of the ultrasound signals.

The term "vibrator ACT" is understood to mean a mechanical actuator capable of generating a shear wave being propagated in the tissue. This shear wave is generated by applying a pulse displacement to transducer US which is positioned close to tissue 5.

Transducer US emits ultrasound signals which are propagated in tissue 5. These ultrasound signals may be monofrequency to follow the propagation of the shear wave. Alternatively, multi-frequency pulses may be used to measure the ultrasound attenuation parameter.

According to method 60 of implementation of the invention, the first viscoelastic parameter is determined by pulse elastography during step ELA, using the technology called Vibration Controlled Transient Elastography (VCTE). This step is implemented using device 3. Vibrator ACT generates a shear wave by applying a pulse displacement of transducer US, wherein said shear wave is propagated in the tissue to be characterised. The mono-frequency ultrasound signals generated by transducer US are used to monitor the propagation of the shear wave. This method enables parameters such as the speed of propagation of the shear wave to be deduced. For example, in the case of the human liver this method enables the elasticity of the organ to be measured, and therefore information concerning the fibrosis to be obtained.

Device 3 also enables step ATT of method 60 according to the invention to be implemented. During this step method 1 is implemented, which amounts to sending a sequence of multi-frequency ultrasound pulses, and measuring the reflected signals to determine the attenuation parameters at the various frequencies. During step ATT of method 60 only transducer US is active.

Advantageously, device 3 enables method 60 to be implemented, and pulse elastography measurements and ultrasound attenuation measurements to be inserted. The possibility of making these two measurements in series, as described by method 60, with the same device, enables the duration of the examinations to be reduced, whilst also reducing the impact on the lives of the patients.

In addition, in the case of the human liver simultaneous assessment of the steatosis and of the fibrosis enables a complete diagnosis to be made.

Figure 7:
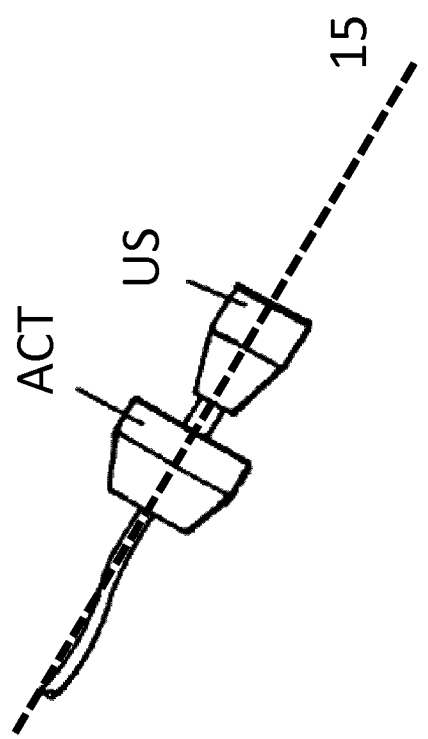
FIG. 7 shows a representation of the probe of the device of FIG. 6.

FIG. 7 shows an example of probe PRO of device 3 in which vibrator ACT and transducer US are securely attached to one another. In addition, vibrator ACT and transducer US have a common axis of symmetry 15, ensuring that the direction of propagation of the shear wave is parallel to the direction of propagation of the ultrasound signals. This condition of parallelism is necessary to measure correct values of the speed of propagation of the shear wave.

The invention claimed is:

1. A method for measuring at least one viscoelastic parameter of a human or animal organ, said method comprising:
    positioning a probe including an ultrasound transducer in contact with an outside surface of a viscoelastic medium;
    controlling, with a controller connected to said probe, said probe such that said ultrasound transducer emits a plurality of ultrasound shots that have a frequency greater than 20 kHz, wherein said ultrasound shots are propagated in tissue of the organ to be characterized;
    receiving by the ultrasound transducer and recording in a computer, in communication with the probe, the reflected ultrasound signals, and
    processing by the computer the reflected ultrasound signals to determine at least one viscoelastic parameter of the organ from the recorded ultrasound signals;
    wherein:
    the plurality of ultrasound shots emitted by the ultrasound transducer is formed by at least one group of ultrasound shots;
    said at least one group of ultrasound shots emitted by the ultrasound transducer is formed by the repetition at a rate (Pulse Repetition Frequency) PRF2 of $M_K$ sets of ultrasound shots, wherein $M_K$ is greater than or equal to 2;
    each of said $M_K$ sets consists of N ultrasound shots emitted by the ultrasound transducer, wherein N is greater than or equal to 2, and wherein PRF1 is the rate of emission of the N shots, wherein PRF1 is greater than PRF2;
    the N ultrasound shots emitted by the ultrasound transducer are distributed over P frequencies, wherein P is between 2 and N, and wherein at least two ultrasound shots emitted by the ultrasound transducer belonging to at least one MK set have different frequencies,
    wherein the measured viscoelastic parameter is an ultrasound attenuation parameter, and wherein the method further comprises determining, by the computer, a coefficient of absorption of the tissue at said different frequencies so that a value of the coefficient of absorption is determined at each one of said different frequencies and providing a measurement of steatosis present in the organ based on the coefficient of absorption determined at each one of said different frequencies.

2. The method according to claim 1, wherein rate PRF2 is greater than or equal to 1 Hz and rate PRF1 is greater than or equal to 1 kHz.

3. The method according to claim 1, wherein the P different frequencies, and the spectral widths of the N ultrasound shots, are chosen such that they cover the bandwidth of the ultrasound transducer.

4. The method according to claim 3, wherein P is equal to N.

5. The method according to claim 1, wherein $M_K$ is between 10 and 10000, P is between 2 and 11, N is between 2 and 11, PRF2 is between 5 Hz and 500 Hz and PRF1 is between 3 kHz and 10 kHz.

6. The method according to claim 1, wherein Fc is the central frequency of the ultrasound transducer, P is equal to 5, and the chosen frequencies are $0.5*Fc<F1<0.7*Fc$, $0.7*Fc<F2<0.9*Fc$, $0.9*Fc<F3<1.1*Fc$, $1.1*Fc<F4<1.3*Fc$, $1.3*Fc<F5<1.5*Fc$.

7. A method for measuring at least one viscoelastic parameter of a human or animal organ, said method comprising:
    measuring a viscoelastic parameter of the organ by pulse elastography; and
    measuring a parameter of attenuation of the ultrasound signals according to claim 1.

8. A device for implementation of the method according to claim 1, wherein said device includes:

a probe including an ultrasound transducer adapted to emit and receive ultrasound signals, in real time, and adapted to be positioned in contact with an outside surface of the viscoelastic medium;

a controller connected to said probe and adapted to control said ultrasound transducer for the emission of a plurality of ultrasound shots, wherein said plurality of ultrasound shots is formed by at least one group of ultrasound shots, wherein said at least one group of ultrasound shots is formed by the repetition at a rate PRF2 of $M_K$ sets of ultrasound shots, and wherein $M_K$ is greater than or equal to 2; wherein each of said $M_K$ sets is composed of N ultrasound shots, wherein N is greater than or equal to 2, and wherein PRF1 is the rate of emission of the N shots, wherein PRF1 is greater than PRF2; wherein the N ultrasound shots are distributed over P frequencies, wherein P is between 2 and N, and wherein at least two ultrasound shots belonging to at least one $M_K$ set have different frequencies;

a computer in communication with the probe and adapted to record and process the reflected ultrasound signals, wherein the processing system is able to determine at least one viscoelastic parameter of organ, wherein the measured viscoelastic parameter is an ultrasound attenuation parameter, and wherein the computer is adapted to determine a coefficient of absorption of the tissue at said different frequencies so that a value of the coefficient of absorption is determined at each one of said different frequencies and to provide a measurement of steatosis present in the organ based on the coefficient of absorption determined at each one of said different frequencies.

9. A device for implementation of the method according to claim 7, said device comprising:

a vibrator adapted to apply to a human or animal organ a low-frequency pulse to generate a shear wave;

a probe including at least one ultrasound transducer adapted to emit and receive ultrasound signals, in real time, and adapted to be positioned in contact with an outside surface of the viscoelastic medium;

a controller connected to said probe and adapted to control said probe for the emission of a plurality of ultrasound shots, wherein said plurality of ultrasound shots is formed by at least one group of ultrasound shots, wherein said at least one group of ultrasound shots is formed by the repetition at a rate PRF2 of $M_K$ sets of ultrasound shots, and wherein $M_K$ is greater than or equal to 2; wherein each of said $M_K$ sets is composed of N ultrasound shots, wherein N is greater than or equal to 2, and wherein PRF1 is the rate of emission of the N shots, wherein PRF1 is greater than PRF2; wherein the N ultrasound shots are distributed over P frequencies, wherein P is between 2 and N, and wherein at least two ultrasound shots belonging to at least one MK set have different frequencies;

a computer in communication with the probe and adapted to record and process the reflected ultrasound signals, wherein the processing system is able to determine at least one viscoelastic parameter of the organ, wherein the measured viscoelastic parameter is an ultrasound attenuation parameter, and wherein the processing system is adapted to determine a coefficient of absorption of the tissue at said different frequencies so that a value of the coefficient of absorption is determined at each one of said different frequencies and to provide a measurement of steatosis present in the organ based on the coefficient of absorption determined at each one of said different frequencies.

* * * * *